US008476031B2

(12) United States Patent
Johnsson et al.

(10) Patent No.: US 8,476,031 B2
(45) Date of Patent: Jul. 2, 2013

(54) METHODS FOR PROTEIN LABELING BASED ON ACYL CARRIER PROTEIN

(75) Inventors: Kai Johnsson, Lausanne (CH); Nathalie George, Vevey (CH)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 461 days.

(21) Appl. No.: 12/647,778

(22) Filed: Dec. 28, 2009

(65) Prior Publication Data
US 2010/0173384 A1 Jul. 8, 2010

Related U.S. Application Data

(62) Division of application No. 10/557,897, filed as application No. PCT/IB2004/001733 on May 19, 2004, now Pat. No. 7,666,612.

(30) Foreign Application Priority Data

May 23, 2003 (EP) .................................... 03405364

(51) Int. Cl.
*G01N 33/53* (2006.01)
*C07K 14/00* (2006.01)
(52) U.S. Cl.
USPC .............................. 435/7.22; 530/350; 514/2
(58) Field of Classification Search
None
See application file for complete search history.

(56) References Cited

U.S. PATENT DOCUMENTS 5,087,563 A 2/1992 Beremand et al.
6,579,695 B1 6/2003 Lambalot et al.

FOREIGN PATENT DOCUMENTS

WO 97/13845 4/1997
WO 02/16583 2/2002

OTHER PUBLICATIONS

Duncombe, W.G., "Fatty acid synthesis in rat adipose tissue", Biochem. J. 106: 179-183 (1968).*
M. Rawlings et al., "The Gene Encoding *Escherichia coli* Acyl Carrier Protein Lies within a Cluster of Fatty Acid Biosynthetic Genes", The Journal of Biological Chemistry, vol. 267, No. 9, pp. 5751-5754, Mar. 25, 1992.
T. Ritsema et al., "Functional analysis of an interspecies chimera of acyl carrier proteins indicates a specialized domain for protein recognition", Mol. Gen. Genet., vol. 257, No. 6, pp. 641-638, Apr. 1998.
M. R. Mofid et al., "Recognition of Hybrid Peptidyl Carrier Proteins/Acyl Carrier Proteins in Nonribosomal peptide Synthetase Modules by the 4'-Phophopantetheinyl Transferases AcpS and Sfp", The Journal of Biological Chemistry, vol. 277, No. 19, pp. 17023-17031, May 10, 2002.

K. V. Gopalan et al., "Inhibition of Acyl-CoA Oxidase by Phenol and its Implication in Measurement of the Enzyme Activity via the Peroxidase-Coupled Assay System", Analytical Biochemistry, vol. 250, No. 1, pp. 44-50, 1997.
X. He et al., "Development of a Scintillation Proximity Assay for β-Ketoacyl-acyl Carrier Protein Synthase III", Analytical Biochemistry, vol. 282, No. 1, pp. 107-114, 2000.
R. P. Hassett et al., "Endpoint Fluorometric Assays for Determining Activities of Carnitine Palmitoyltransferase and Citrate Synthase", Analytical Biochemistry, vol. 287, No. 1, pp. 176-179, 2000.
M. A. Nada et al., "Spectrophotometric Assay of 2,4-Dienoyl Coenzyme A Reductase with 5-Phenyl-2,4-pentadienoyl-Coenzyme A as Substrate", LIPIDS, vol. 29, No. 7, pp. 517-521, 1994.
J. M. Shockey et al., "Identification of Jojoba Seed Acyl-CoA: Fatty Alcohol Acyltransferase by Photolabeling with Acyl-CoA Analog", Plant Lipid Metabolism, Papers Presented at the International Meeting on Plant Lipids, Jun. 26-Jul. 1, 1994, pp. 540-542.
M. Tanaka et al., "Enzymatic production of a α-dehydrobiotin from biotin", Journal of Biotechnology, vol. 5, No. 3, pp. 209-220, 1987.
T. A. Bobik et al., "HPLC Assay for Methylmalonyl-CoA Epimerase", Anal. Bioanal. Chem., vol. 375, No. 3, pp. 344-349, 2003.
A. Chapman-Smith et al., "The enzymatic biotinylation of proteins: a post-translation modification of exceptional specificity", TIBS, vol. 24, No. 9, pp. 359-363, Sep. 1, 1999.
Brown et al., "Probing the mechanism of the *Mycobacterium tuberculosis* beta-Ketoacyl-Acyl Carrier Protein Synthase III mtFabH", The Journal of Biological Chemistry, vol. 280, No. 37, pp. 32539-32547, 2005.
White et al., "The structural biology of type II fatty acid biosynthesis", Annual Review of Biochemistry, vol. 74, pp. 791-831, 2005.
T. Weber et al., "Solution structure of PCP, a prototype for the peptidyl carrier domains of modular peptide synthetases", *Structure* (2000), vol. 8, No. 4, pp. 407-418.
R. Lambalot et al., "A new enzyme superfamily—the phosphopantetheinyl transferases", *Chemistry & Biology* (1996), vol. 3, No. 11, pp. 923-936.

* cited by examiner

*Primary Examiner* — Anand Desai
(74) *Attorney, Agent, or Firm* — New England Biolabs, Inc; Harriet M. Strimpel

(57) ABSTRACT

A method for labeling acyl carrier protein (ACP) fusion proteins with a wide variety of different labels is disclosed. The method relies on the transfer of a label from a coenzyme A type substrate to an ACP fusion protein using a holo-acyl carrier protein synthase (ACPS) or a homologue thereof. The method allows detecting and manipulating the fusion protein, both in vitro and in vivo, by attaching molecules to the fusion proteins that introduce a new physical or chemical property to the fusion protein. Examples of such labels are, among others, spectroscopic probes or reporter molecules, affinity tags, molecules generating reactive radicals, cross-linkers, ligands mediating protein-protein interactions or molecules suitable for the immobilization of the fusion protein.

4 Claims, 2 Drawing Sheets

```
                          SEQUENCE LISTING

<160> NUMBER OF SEQ ID NOS: 8

<210> SEQ ID NO 1
<211> LENGTH: 34
<212> TYPE: DNA
<213> ORGANISM: Artificial Sequence
<220> FEATURE:
<223> OTHER INFORMATION: Foward primer for cloning ACPS into pET-15b

<400> SEQUENCE: 1
tctggtcata tggcaatatt aggtttaggc acgg                              34

<210> SEQ ID NO 2
<211> LENGTH: 37
<212> TYPE: DNA
<213> ORGANISM: Artificial Sequence
<220> FEATURE:
<223> OTHER INFORMATION: Backward primer for cloning ACPS into pET-15b

<400> SEQUENCE: 2
tcaagtctcg agttaacttt caataattac cgtggca                           37

<210> SEQ ID NO 3
<211> LENGTH: 20
<212> TYPE: PRT
<213> ORGANISM: Artificial Sequence
<220> FEATURE:
<223> OTHER INFORMATION: 6xHis extension for ACPS and ACP

<400> SEQUENCE: 3

Met Gly Ser Ser His His His His His His Ser Ser Gly Leu Val Pro
1               5                   10                  15

Arg Gly Ser His
            20

<210> SEQ ID NO 4
<211> LENGTH: 31
<212> TYPE: DNA
<213> ORGANISM: Artificial Sequence
<220> FEATURE:
<223> OTHER INFORMATION: Forward primer for cloning ACP into pEt-15b

<400> SEQUENCE: 4
gtcggtatca tatgagcact atcgaagaac g                                 31

<210> SEQ ID NO 5
<211> LENGTH: 31
<212> TYPE: DNA
<213> ORGANISM: Artificial Sequence
<220> FEATURE:
<223> OTHER INFORMATION: Backward primer for cloning ACP into pEt-15b

<400> SEQUENCE: 5
tcatgcggat ccttacgcct ggtggccgtt g                                 31
```

```
<210> SEQ ID NO 6
<211> LENGTH: 15
<212> TYPE: PRT
<213> ORGANISM: Artificial sequence
<220> FEATURE:
<223> OTHER INFORMATION: HA epitope extension for ACP

<400> SEQUENCE: 6

Thr Ser Arg Ser Tyr Pro Tyr Asp Val Pro Asp Tyr Ala Arg Trp
1               5                   10                  15

<210> SEQ ID NO 7
<211> LENGTH: 11
<212> TYPE: PRT
<213> ORGANISM: Artificial sequence
<220> FEATURE:
<223> OTHER INFORMATION: sequence connecting Aga2p and ACP

<400> SEQUENCE: 7

Phe Val Asp Glu Met Leu Tyr Phe Gln Gly Met
1               5                   10

<210> SEQ ID NO 8
<211> LENGTH: 12
<212> TYPE: PRT
<213> ORGANISM: Artificial Sequence
<220> FEATURE:
<223> OTHER INFORMATION: HA Epitope extension for Aga2p ACP fusion
      protein

<400> SEQUENCE: 8

Gln Ala Tyr Pro Tyr Asp Val Pro Asp Tyr Ala Gly
1               5                   10
```

METHODS FOR PROTEIN LABELING BASED ON ACYL CARRIER PROTEIN

This application is a divisional of Ser. No. 10/557,897, filed Nov. 22, 2005 now U.S. Pat. No. 7,666,612, which is a 371 U.S. national stage of International Application No. PCT/IB2004/001733 filed May 19, 2004, herein incorporated by reference in their entirety.

FIELD OF THE INVENTION

The present invention relates to methods of transferring a label from a substrate to a fusion protein comprising a protein of interest and an acyl carrier protein or a fragment thereof, and in particular to methods which further comprise detecting and/or manipulating the labeled fusion protein.

BACKGROUND OF THE INVENTION

Progress in understanding complex biological systems depends on characterizing the underlying interactions of biomolecules, in particular proteins. While the DNA sequencing of an increasing number of organisms has identified their open reading frames (ORF), the possibilities to characterize the corresponding proteins in vivo and in vitro are limited. Most strategies that aim at realizing this objective are based on the construction of a fusion protein that either allows the purification of the fusion for in vitro applications or allows following the protein in vivo. Examples for such tags include the 6xHis tag, glutathione S transferase, maltose binding protein, epitope tags, yeast-two hybrid system, $O^6$-alkylguanine-DNA alkyltransferase, split-ubiquitin, and green fluorescent protein (GFP) fusion proteins. However, all these techniques have various limitations or disadvantages.

Gehring et al. (1997) and Lambalot and Walsh (1995) describe the use of *E. coli* holo acyl carrier protein synthase (ACPS) to catalyze the posttranslational modification of apo-acyl carrier protein (apo-ACP) by attaching the cofactor 4'-phosphopantetheine (P-pant) to a conserved serine residue in vitro, yielding holo-ACP. The source of P-pant is coenzyme A. Gehring et al. (1997) demonstrate furthermore that, by using coenzyme A analogs, which are modified in the P-pant part but still able to serve as substrates for ACPS, holo-ACP's with modified P-pants as cofactor are obtained.

Isolated phosphopantetheinyl transferases such as ACPS are described in International Patent Application WO 97/13845.

A method of transferring a label to $O^6$-alkylguanine-DNA alkyltransferase (AGT) fusion proteins, and the use of this method for the detection of AGT fusion proteins is described in International Patent Application WO 02/083937.

SUMMARY OF THE INVENTION

The invention relates to a method for detecting and/or manipulating a protein of interest, which comprises contacting a fusion protein comprising protein of interest and an acyl carrier protein (ACP) or a fragment thereof with a labeled coenzyme A (CoA) type substrate and a holo-acyl carrier protein synthase (ACPS) or a homologue thereof so that the ACPS transfers the label to the fusion protein, and optionally detecting and/or further manipulating the labeled fusion protein obtained, using the label in a system designed for recognising and/or handling the label.

Furthermore the invention relates to the use of a fusion protein comprising protein of interest and an ACP or a fragment thereof in such a method. In particular, the method of the invention is used for purifying or immobilizing a protein of interest, or for continuously monitoring a protein of interest in vitro or in vivo due to the label attached to it in the method of the invention.

The protein of interest incorporated into the fusion protein of the invention may be of any kind, which includes proteins, polypeptides and peptides of any length and both with and without secondary, tertiary or quaternary structure.

The particular labeled coenzyme A (CoA) type substrates used in the method of the invention are obtainable from CoA or modified CoA by attachment of a linker with at least one reactive site for further attachment of a label, i.e. a detectable marker. The invention also relates to such novel labeled coenzyme A (CoA) type substrates, to methods of manufacture thereof, to intermediates useful in the synthesis of such novel CoA type substrates, and to their use in the method of the invention.

Figure 1:
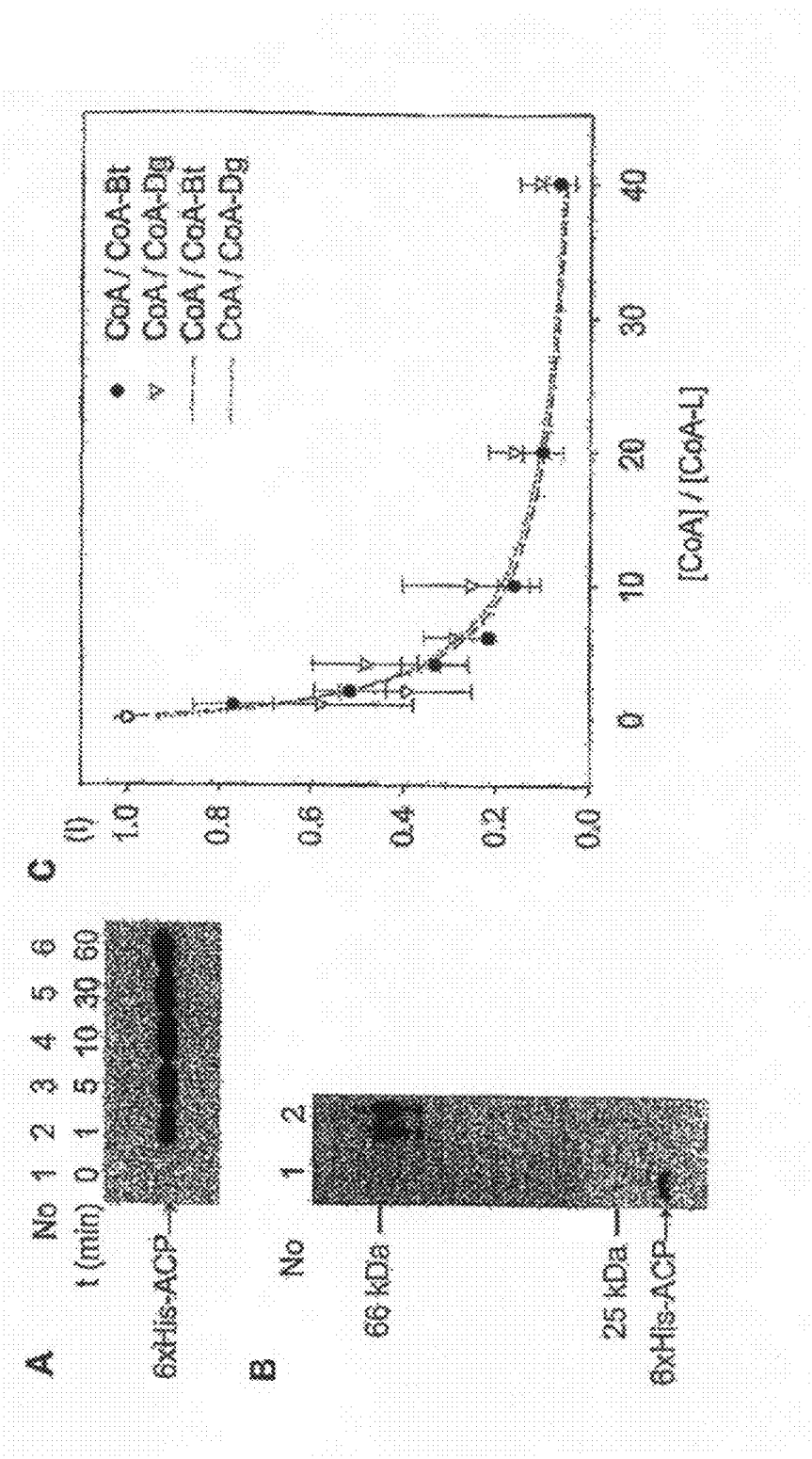
FIG. 1.
Figure 2:
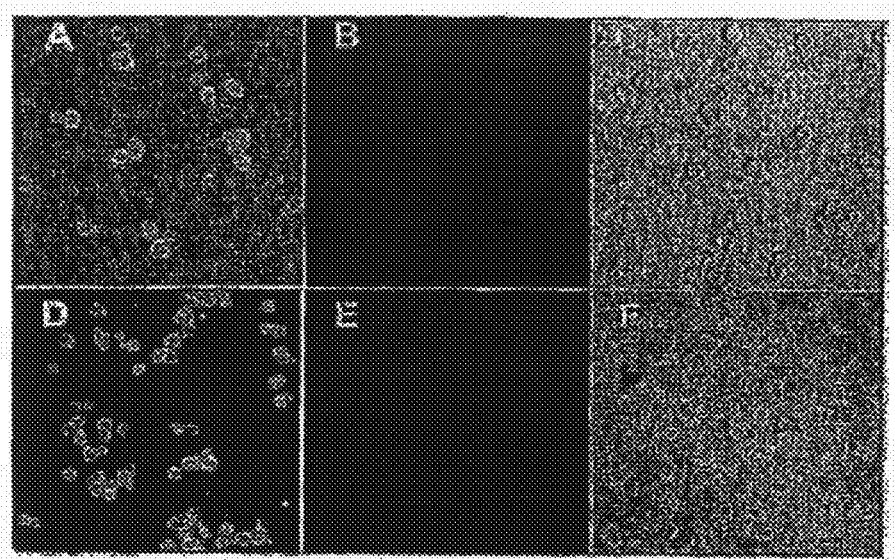

(A) Analysis of the reaction of 6xHis-ACP (1 µM), 6xHis-ACPS (0.2 µM) and CoA-Bt (5 µM). At indicated times (t) aliquots are removed from the reaction mixture and biotinylation of 6xHis-ACP probed by Western blotting using a streptavidin-peroxidase conjugate.

(B) Quantification of biotinylation of 6xHis-ACP: 6xHis-ACP (3 µM), 6xHisACPS (5 µM) and CoA-Bt (10 µM) are incubated for 30 min, dialyze and aliquots of the sample are incubated with streptavidin and applied to SDS-PAGE (lane No. 2). The formation of a stable biotin-streptavidin complex leads to a gel shift of biotinylated protein. The amount of biotinylation is estimated by comparing the band intensity of 6xHis-ACP in lane No. 2 with that of a sample containing identical concentrations of 6xHis-ACP but no streptavidin (lane No. 1).

(C) Competition assay between CoA and CoA-Bt or CoA-Dg as ACPS substrates: 6xHis-ACP (0.4 µM), 6xHis-ACPS (0.4 µM), CoA-Bt or CoA-Dg (2 µM) and varying concentrations of CoA (0-80 µM) are incubated for 30 min and the degree of labeling determined by Western blotting. The relative signal intensities (I) in the Western blots are plotted against [CoA]/[CoA-L](L=label) and fitted to the equation I=A/(1+Bx), where x represents [CoA]/[CoA-L], A an unspecified constant and B the ratio $(k_{cat}/K_M)_{CoA}/(k_{cat}/K_M)_{CoA-L}$. These experiments yield ratios of the specificity constants of 0.48 for $(k_{cat}/K_M)_{CoA}/(k_{cat}/K_M)_{CoA-Bt}$ and of 0.35 for $(k_{cat}/K_M)_{CoA}/(k_{cat}/K_M)_{CoA-Dg}$, revealing no significant discrimination between free and derivatized CoA.

FIG. 2

(A-F) Labeling of ACP fusion proteins on cell surfaces of yeast. Fluorescence micrographs of yeast cells expressing Aga2-ACP which are labeled with either Cy3 (A) or biotin followed by streptavidin-coated quantum dots (D). (B) as (A) and (E) as (D) but with cells not expressing AGA2-ACP: (C) and (F) are the transmission micrograph of the same samples as in (B) and (D), respectively. These experiments indicate that only the yeast cells expressing Aga2p-ACP are labelled.

DETAILED DESCRIPTION OF THE INVENTION

The invention relates to a method for detecting and/or manipulating a protein of interest, which comprises contacting a fusion protein comprising protein of interest and an acyl carrier protein (ACP) or a fragment thereof with a labeled coenzyme A (CoA) type substrate and a holo-acyl carrier protein synthase (ACPS) or a homologue thereof so that the ACPS transfers the label to the fusion protein, and optionally detecting and/or further manipulating the labeled fusion protein obtained using the label in a system designed for recognising and/or handling the label.

ACP or ACP domains act as carriers in the biosynthesis of fatty acids, polyketides and in non-ribosomal peptide synthesis. ACP is posttranslationally modified by holo-acyl carrier protein synthase (ACPS) which transfers the 4-phosphopantetheine cofactor from the coenzyme A to a conserved serine residue of ACP. ACPSs are also called phosphopante-theinyl transferases. It has been shown that ACPSs possesses a relatively low substrate specificity concerning modifications of CoA at the thiol group of the phosphopantetheinyl moiety of CoA. Taking advantage of this, ACP fusion proteins can be specifically labeled by incubation with ACPS and a CoA derivative that carries the label via the phospho-pantetheinyl moiety. The label is thus transferred with the phosphopantetheinyl moiety to the conserved serine residue of the ACP. The labelling is independent of the nature of the fusion protein.

The terms ACP and ACPS here stand for any pair of proteins in which one of the two (the ACP) is an acceptor for a phosphopantetheinyl derivative that originates from a CoA derivative and the other one (the ACPS) catalyzes the transfer of the phosphopantetheinyl derivative to this ACP.

The terms ACPS and phosphopantetheinyl transferase are used interchangeably herein despite the fact that a number of phosphopantetheinyl transferases homologous to ACPS from E. coli modify proteins that do not participate in fatty acid synthesis but rather in the biosynthesis of natural products (Lambalot et al., 1996). Examples for such phospho-pantetheinyl transferases are: EntD, participating in enterobactin synthesis; Sfp and Psf-1, participating in surfactin biosynthesis; Gsp, participating in gramidicin S biosynthesis; LYS5, participating in lysine biosynthesis; Bli, participating in bacitracin biosynthesis; Lpa-14, participating in iturin A biosynthesis; and NshC, participating in nosiheptide biosynthesis. This invention includes the use of all ACPSs in the labeling scheme that are homologous to the ACPS from E. coli.

The term ACP stands for any protein that will be posttranslationally phosphopante-theinylated by ACPS from E. coli or any ACPS homologous to the ACPS from E. coli as defined by Lambalot et al. (1996). This includes proteins not only participating in fatty acid synthesis but also in polyketide synthesis, non-ribosomal peptide synthesis, amino acid synthesis and depsipeptide synthesis. In addition to the posttranslational modification by ACPS these proteins have also in common that they form acyl-pantetheinyl thiolesters with different substrates and that the phosphopantetheinyl moiety is attached to a serine residue. In their natural function the ACPs might be the domain of a multi-functional enzyme (as in type I fatty acid synthases) or a separate protein (as in type II fatty acid synthases).

"Detecting" means observing the label and the protein of interest attached to it based on the properties of a label in a system designed for observing the label, and includes recognising the particular label, finding the label in a particular environment due to the properties of the label, optionally quantifying the label and the protein attached to it, and optionally determining the properties of the micro-environment of the label, and the like. "Manipulating" means handling the label and the protein of interest attached to it, and includes handling the label and the protein of interest attached to it based on the properties of a label in system designed for handling the label, and includes separating from a chemical or biological environment, introducing into another chemical or biological environment, purifying, i.e. separating from unwanted side products and impurities, immobilizing by reaction of the label with a solid carrier, contacting with chemical or biological reagents so as to modify the properties of the label and/or of the protein of interest, and the like.

The method disclosed herein is generally applicable to a range of applications and is capable of specifically and covalently labeling fusion proteins with (1) labels which are capable of sensing and inducing changes in the environment of the labeled fusion protein, (2) labels which aid in manipulating the fusion protein by the physical and/or chemical properties specifically introduced by the label to the fusion protein and/or (3) labels which aid in purification of the fusion protein through the properties introduced by the label. The method disclosed herein can be used to label ACP fusion proteins both in vitro and in vivo, e.g. in cells.

Furthermore the invention relates to the use of a fusion protein comprising protein of interest and an ACP or a fragment thereof in such a method. In particular, the method of the invention is used for purifying or immobilizing a protein of interest, or for continuously monitoring a protein of interest in vitro or in vivo due to the label attached to it in the method of the invention.

In one aspect, the present invention provides a method for continuously monitoring a protein of interest in vitro or in vivo, wherein a fusion protein comprising protein of interest and an acyl carrier protein (ACP) or a fragment thereof is contacted with a labeled coenzyme A (CoA) type substrate and a holo-acyl carrier protein synthase (ACPS) or a homologue thereof so that the ACPS transfers the label to the fusion protein, and the label is observed in a system designed for recognising the label.

In a further aspect, the present invention provides a method for manipulating a protein of interest in vitro or in vivo, wherein a fusion protein comprising protein of interest and an acyl carrier protein (ACP) or a fragment thereof is contacted with a labeled coenzyme A (CoA) type substrate and a holo-acyl carrier protein synthase (ACPS) or a homologue thereof so that the ACPS transfers the label to the fusion protein, and the fusion protein is manipulated based on the physical and/or chemical properties of the label.

In a particular aspect, the physical and/or chemical properties of the label allow efficient purification of the labeled fusion protein, and the present invention accordingly provides a method of purifying a protein of interest by performing the steps of the method of the invention, using the physical and/or chemical properties of the label for purification, and cleaving the fusion protein thereafter providing pure protein of interest.

In a further aspect, the present invention provides a method of immobilizing a fusion protein comprising protein of interest and an acyl carrier protein (ACP) or a fragment thereof on a solid support, the method comprising contacting the fusion protein with a labeled coenzyme A (CoA) type substrate which is attached or attachable to a solid support, wherein the holo-acyl carrier protein synthase (ACPS) transfers the label so that it is covalently bonded to the ACP fusion protein which thereby is attached or can be subsequently attached to the solid support. In particular embodiments of the invention in which the label is not initially attached to the solid support, the method may involve the further step of contacting the labeled ACP fusion protein with the solid support so that it becomes immobilized on the solid support. In these preferred embodiments of the invention, the label may be covalently attached to the solid support, either when the label is transferred or in a subsequent reaction, or may be one member of a specific binding pair, the other member of which is attached or attachable to the solid support, either covalently or by any other means, e.g. using the specific binding pair of biotin and avidin or streptavidin.

In a further aspect, the present invention provides a method to label ACP fusion proteins both in vivo as well as in vitro. The term in vivo labeling of an ACP fusion protein includes labeling in all compartments of a cell as well as of ACP fusion proteins pointing to the extracellular space. If the labeling of the ACP fusion protein is done in vivo and the protein fused to the ACP is a plasma membrane protein, the ACP part of the fusion protein can be either attached to the cytoplasmic or the extracellular side of the plasma membrane. If the labeling is done in vitro, the labeling of the fusion protein can be either performed in cell extracts or with purified or enriched forms of the ACP fusion protein.

The present invention is based on the realization that specific attachment of a label to a desired protein could be carried out by constructing a fusion protein between that protein of interest and the acyl carrier protein (ACP) or a fragment thereof.

In a preferred application, the acyl carrier protein or "ACP" has the property of being modified by the holo-acyl carrier protein synthase or "ACPS" in a way that labeled 4'-phosphopantetheine is transferred from the appropriate coenzyme A ("CoA") to a serine residue of ACP or a fragment thereof forming part of the fusion protein. In preferred embodiments, ACP is, for example, *E. coli* acyl carrier protein which is described in Rawling and Cronan, 1992, and references therein. However, other acyl carrier proteins (ACP) are known and may be used in the invention, e.g. ACP from *Streptomyces* species described in Gehring et al., 1997, or any ACP having the property of being modified by ACPS defined above in the presence of appropriately labeled CoA. In the present invention, ACP also includes variants of a wild-type ACP which may differ by virtue of one or more amino acid substitutions, deletions or additions, but which still retain the property of serving as an acceptor for labeled 4'-phosphopantetheine in the reaction catalyzed by ACPS. Other variants of ACP may be chemically modified using techniques well known to those skilled in the art. ACP variants may be produced using protein engineering techniques known to the skilled person and/or using molecular evolution to generate and select new acceptor sequences for transfer of labeled 4'-phosphopantetheine in the reaction catalyzed by ACPS. ACP fragments are those which contain the serine residue to which the phosphopantetheine derivative is attached, and which retain the function to accept such phosphopantetheine derivative.

In preferred embodiments, the ACPS is, for example, *E. coli* holo-acyl carrier protein synthase which is described in Lambalot and Walsh, 1995, and references therein. However, other holo-acyl carrier protein synthases are known, such as ACPS from *Bacillus subtilis* described in Lambalot et al., 1996, or any form of the protein which can be employed in the present invention provided that they have the property of modifying ACP defined above in the presence of appropriately labeled CoA. These ACPSs are also known as phosphopantetheinyl transferases as described in Lambalot et al., 1996, and the present invention includes the use of this general class of enzymes. In the present invention, holo-acyl carrier protein synthases also includes variants of a wild-type ACPS which may differ by virtue of one or more amino acid substitutions, deletions or additions, but which still retain the property of transferring labeled 4'-phosphopantetheine specifically to the ACP fusion protein. Other variants of ACPS may be chemically modified using techniques well known to those skilled in the art. ACPS variants may be produced using protein engineering techniques known to the skilled person and/or using molecular evolution to generate and select new specificities for transfer of labeled 4'-phosphopantetheine to different acceptor sequences.

For the labeling of ACP fusion proteins by ACPS a number of considerations are advantageously taken into account. Most importantly, the labeling of the ACP fusion protein relies on the presence of the ACP part of the ACP fusion protein in its apo form before labeling. If the ACP fusion protein is expressed in a host that possesses an endogenous ACPS that accepts this ACP fusion protein as a substrate for posttranslational modification the ACP fusion protein can be at least partially blocked for the desired modification. To minimize this unwanted modification of ACP fusion proteins different solutions are proposed. Firstly, an ACP is chosen which is not efficiently modified by the ACPS of the host, i.e. the ACP is orthogonal to the biochemistry of the host. For example, the ACP from *E. coli* is not modified to a significant extent by the human ACPSs when expressed as a fusion protein in human cells (see FIG. 3). Secondly, overexpression of the ACP fusion protein will lead to the predominant formation of apo-ACP in ACP fusion proteins. For example, overexpression of 6xHis-ACP from *E. coli* in *E. coli* leads to the formation of mostly apoLACP in 6xHis-ACP, although the endogenous ACPS is present in these cells.

For the labeling reaction, ACP fusion proteins have also to be contacted with both the corresponding ACPS and the CoA derivative. This implies that for in vivo applications the ACP fusion protein is either presented on the surface of the cell or the ACPS and the CoA derivative are introduced into the cell of interest using techniques such as microinjection.

In the present invention, the reference to the protein part of the fusion protein with the ACP is intended to include proteins, polypeptides and peptides of any length and both with and without secondary, tertiary or quaternary structure, and preferably consists of at least twelve amino acids and up to 2000 amino acids, preferably between 50 and 1000 amino acids. The protein of interest according to the invention is selected from the group consisting of enzymes, DNA-binding proteins, transcription regulating proteins, membrane proteins, nuclear receptor proteins, nuclear localization signal proteins, protein cofactors, antibodies, membrane pump proteins, membrane channel proteins, membrane carrier proteins, motor proteins, proteins involved in signal transduction, nuclear proteins, ribosomal proteins, small monomeric GTPases, ATP-binding cassette proteins, intracellular structural proteins, proteins with sequences responsible for targeting proteins to particular cellular compartments, proteins generally used as labels or affinity tags, and domains or subdomains of the aforementioned proteins. The ACP fusion protein may consist of one or more, e.g. one, two or three, proteins of interest fused to ACP at the N-, C- or N- and C-terminal of ACP.

More particularly, the protein of interest according to the invention is selected from the group consisting of enzymes, e.g. transferases (EC 2), more specific a transferase transferring an alkyl or aryl group other than a methyl group (EC 2.5), in particular a glutathione transferase (EC 2.5.1.18), or a kinase, that is a transferase transferring phosphorus containing groups (EC 2.7), in particular a kinase with an alcohol group as acceptor (EC 2.7.1), such as a protein kinase with serine and threonine as the phosphorylated target sites in the substrate protein, e.g. casein kinase from yeast (EC 2.7.1.37), or a tyrosine protein kinase (EC 2.7.1.112); or e.g. oxidoreductases (EC 1), more specific an oxidoreductase acting on peroxide as acceptor (EC 1.11), in particular the enzyme cytochrome C peroxidase (EC 1.11.1.5); or e.g. hydrolases (EC 3), more specific a hydrolase acting on an ester bond (EC 3.1), in particular a phosphoric monoester hydrolase (EC 3.1.3), such as a protein phosphoric monoester hydrolase; or a hydrolase hydrolysing peptide bonds, also known as peptidase or protease (EC 3.4), in particular a caspase;

DNA-binding proteins, more specific transcription repressor proteins which are protein factors inhibiting mRNA synthesis, specifically a protein factor inhibiting mRNA synthesis in *E. coli*, in particular the DNA-binding domain of the LexA protein;

transcription regulating proteins, more specific transcription repressor proteins, in particular transcription repressor proteins containing a tryptophan/aspartate repeat structure, membrane proteins, e.g. membrane proteins showing at least one transmembrane helix, more specific membrane proteins from the endoplasmatic reticulum (ER) membrane, in particular membrane proteins being active in protein translocation into the ER, such as the ER transmembrane protein Sec62;

or e.g. a protein from the family of 7-transmembrane helix (7-TM) proteins, more specific a 7-TM protein being a G-protein coupled receptor (GPCR), in particular those that bind macromolecular ligands with a molecular weight above 1 kDa, such as a mammalian, e.g. human, neurokinin-1-receptor (NK1);

or e.g. transmembrane ion channel proteins from the cell membrane, in particular ligand gated ion channel proteins, more specific a ligand gated ion channel proteins sensitive to serotonin, such as the serotonin receptor 5-HT3;

or e.g. membrane receptors other than ion channels and G-protein coupled receptors; or e.g. peroxisomal membrane proteins, in particular from yeast, such as the protein Pex15;

nuclear receptor proteins, e.g. nuclear receptor proteins from the family of transcription factors, more specific nuclear receptor proteins from the family of ligand inducible transcription factors, in particular a nuclear receptor from the family of steroid, e.g. estrogen, receptors, such as the human estrogen receptor hER;

nuclear localization signal proteins, such as the nuclear localization signal from the Simian Virus 40 (SV40);

protein cofactors, e.g. proteins containing an ubiquitin sequence in their genetic structure; small monomeric GTPases, more specific membrane-adherent small monomeric GTPases, e.g. a member of the Ras family;

ATP-binding cassette (ABC) proteins, e.g. a multiple drug resistance protein; intracellular structural proteins, more specifically proteins of the cytoskeleton, more specifically human cytoplasmic β-actin;

proteins with sequences responsible for targeting proteins to particular cellular compartments, e.g. to the Golgi apparatus, the endoplasmatic reticulum (ER), the mitochondria, the plasma membrane or the peroxisome;

proteins generally used as labels or affinity tags, e.g. fluorescent proteins giving a fluorescent signal on excitation with UV or visible radiation, in particular fluorescent proteins from the family known as green fluorescent proteins (GFP), such as the fluorescent protein known as enhanced cyano fluorescent protein (ECFP);

and domains or subdomains of the aforementioned proteins.

Furthermore, the protein of interest according to the invention is selected according to source. In particular, proteins of interest are those present in human species, mice, rats, other higher mammals, eukaryotic species, bacterial species, e.g. *salmonella*, more specific *salmonella typhi* or *salmonella typhimurium*, mycobacteria, more specific *mycobacterium tuberculensis*, or *staphylococci*, more specific *staphylococcus aureus*, or from a viral source, e.g. human immunodeficiency virus (HIV), human influenza virus, hepatitis virus, or corona viruses.

Furthermore, the protein of interest is selected according to its role in a certain disease, such as cancer, cardiovascular diseases, mental disorders, Alzheimer, obesity, viral infections, and bacterial infections.

In a particular embodiment of the invention the fusion proteins are made from *E. coli* ACP or variants of such ACP DNA on the one side and proteins of interest (as listed above) encoding sequences either attached to the N-terminal (N) or the C-terminal (C) side or N- and C-terminal side of the ACP DNA sequence, leading to the fusion proteins of the invention. Fusion proteins may further contain suitable linkers, e.g. linkers which may be susceptible to enzyme cleavage under suitable conditions, between ACP and the protein of interest and/or between two proteins of interest in a fusion protein. Examples of such linkers are those which are cleavable at the DNA stage by suitable restriction enzymes, e.g. AGATCT cleavable by Bgl II, and/or linkers cleavable by suitable enzymes at the protein stage, e.g. tobacco etch virus NIa (TEV) protease.

Fusion proteins may be expressed in prokaryotic hosts, preferably *E. coli*, or eukaryotic hosts, e.g. yeast, fungal, insect or mammalian cells.

The invention also relates to novel fusion protein comprising a protein of interest and an ACP or a fragment thereof.

In the present invention, the labeled CoA type substrate is preferably a labeled coenzyme A derivative possessing the following general formula (I):

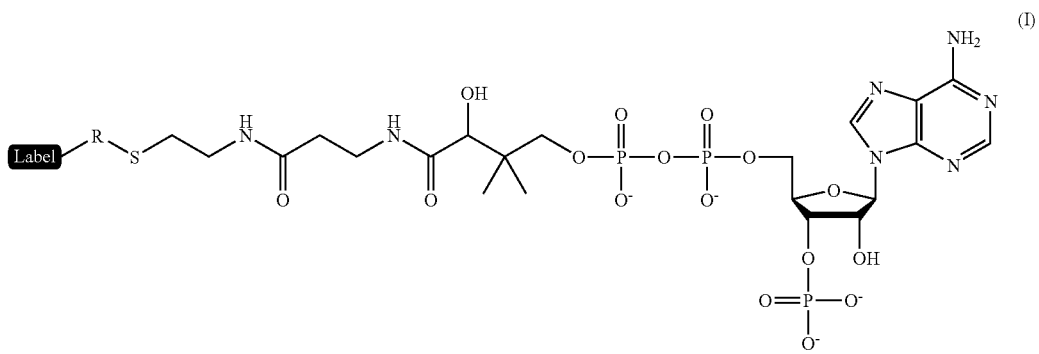

or the following general formula (II):

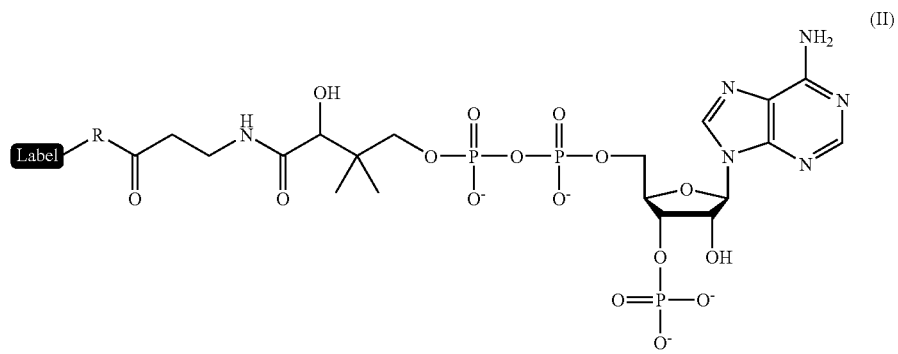

wherein
R is a linker group bridging the coenzyme A and the label; and "Label" is a label molecule suitable for the detection, purification and/or manipulation of the fusion protein as described herein.

However, the invention is not restricted to the substrates of formula (I) or (II) since a wide range of other substrates can be used for a transfer of a label to ACP fusion proteins. For example, substitutions of the purine part, modifications of the sugar moiety or of the panthetheinylic acid moiety of a compound of formula (I) are considered.

A linker group R in a compound of formula (I) or (II) is a flexible linker connecting a label to the coenzyme A. Linker units are chosen in the context of the envisioned application, i.e. in the transfer of the label to a fusion protein comprising ACP. They also increase the solubility of the substrate in the appropriate solvent. The linkers used are chemically stable under the conditions of the actual application. The linker R does not interfere with the reaction with ACP nor with the detection of the label, but may be constructed such as to be cleaved at some point in time after the reaction of the coenzyme A type substrate with the fusion protein comprising ACP.

A linker group R is a straight or branched chain alkylene group with 1 to 300 carbon atoms, wherein optionally
(a) one or more carbon atoms are replaced by oxygen, in particular wherein every third carbon atom is replaced by oxygen, e.g. a poylethylenoxy group with 1 to 100 ethylenoxy units;
(b) one or more carbon atoms are replaced by nitrogen carrying a hydrogen atom, and the adjacent carbon atoms are substituted by oxo, representing an amide function —NH—CO—;
(c) one or more carbon atoms are replaced by oxygen, and the adjacent carbon atoms are substituted by oxo, representing an ester function —O—CO—;
(d) the bond between two adjacent carbon atoms is a double or a triple bond, representing a function —CH═CH— or —C≡C—;
(e) one or more carbon atoms are replaced by a phenylene, a saturated or unsaturated cycloalkylene, a saturated or unsaturated bicycloakylene, a bridging heteraromatic or a bridging saturated or unsaturated heterocyclyl group;
(f) two adjacent carbon atoms are replaced by a disulfide linkage —S—S—;
or a combination of two or more, especially two, alkylene and/or modified alkylene groups as defined under (a) to (f) hereinbefore, optionally containing substituents.

Substituents considered are e.g. lower alkyl, e.g. methyl, lower alkoxy, e.g. methoxy, lower acyloxy, e.g. acetoxy, or halogenyl, e.g. chloro.

Further substituents considered are e.g. those obtained when an α-amino acid is incorporated in the linker R wherein carbon atoms are replaced by amide functions —NH—CO— as defined under (b). In such a linker part of the carbon chain of the alkylene group R is replaced by a group —(NH—CHR'—CO)$_n$— wherein n is between 1 and 100 and R' represents a varying residue of an α-amino acid.

A further substituent is one which leads to a photocleavable linker R, e.g. an o-nitrophenyl group. In particular this substituent o-nitrophenyl is located at a carbon atom adjacent to a amide bond, e.g. in a group —NH—CO—CH$_2$—CH(o-nitrophenyl)-NH—CO—.

A phenylene group replacing carbon atoms as defined under (e) hereinbefore is e.g. 1,2-, 1,3-, or preferably 1,4-phenylene. A saturated or unsaturated cycloalkylene group replacing carbon atoms as defined under (e) hereinbefore is e.g. cyclopentylene or cyclohexylene, or also cyclohexylene being unsaturated e.g. in 1- or in 2-position. A saturated or unsaturated bicycloalkylene group replacing carbon atoms as defined under (e) hereinbefore is e.g. bicyclo[2.2.1]heptylene or bicyclo[2.2.2]octylene, optionally unsaturated in 2-position or doubly unsaturated in 2- and 5-position. A heteroaromatic group replacing carbon atoms as defined under (e) hereinbefore is e.g. triazolidene, preferably 1,4-triazolidene, or isoxazolidene, preferably 3,5-isoxazolidene. An saturated or unsaturated heterocyclyl group replacing carbon atoms as defined under (e) hereinbefore is e.g. 2,5-tetrahydrofuranediyi or 2,5-dioxanediyl, or isoxazolidinene, preferably 3,5-isoxazolidinene.

Preferred linker groups R are, for example, a flexible linker such as a alkyl chain of 1 to 20 carbon atoms, optionally substituted by methyl, methoxy or acetoxy groups, or a polyethylene glycol chain consisting of 1 to 20 ethylenoxy groups.

The label part of the substrate can be chosen by those skilled in the art dependent on the application for which the fusion protein is intended. Examples of labels include:
(1) A spectroscopic probe such as a fluorophore, a chromophore, a magnetic probe or a contrast reagent, or also a probe useful in electron microscopy;
(2) A radioactively labeled molecule;
(3) A molecule which is one part of a specific binding pair which is capable of specifically binding to a partner. Such specific binding pairs are well known in the art and include, for example, biotin, which can bind to avidin or streptavidin;

(4) A molecule that is suspected to interact with other biomolecules;
(5) A library of molecules that are suspected to interact with other biomolecules;
(6) A molecule which is capable of crosslinking to other biomolecules as known to those skilled in the art, e.g. as described by Nadeau et al., 2002;
(7) A molecule which is capable of generating hydroxyl radicals upon exposure to $H_2O_2$ and ascorbate such as a tethered metal-chelate, e.g. as described by Hod et al., 2002;
(8) A molecule which is capable of generating reactive radicals upon irradiation with light such as malachite green, e.g. as described by Jay et al. 1999;
(9) A molecule covalently attached to a solid support, where the support may be a glass slide, a microtiter plate or any polymer in general known to those proficient in the art;
(10) A nucleic acid or a derivative thereof capable of undergoing base-pairing with its complementary strand;
(11) A lipid or other hydrophobic molecule with membrane-inserting properties;
(12) A biomolecule with desirable enzymatic, chemical or physical properties;
(13) A molecule possessing a combination of any of the properties listed above.

The use of a labeled CoA derivative, wherein the phosphopantetheinyl moiety carries a detectable label which can be transferred to the ACP fusion protein, such as a fluorophore, a chromophore, a magnetic probe, a radioactively labeled molecule or any other spectroscopic probe, allows the invention to be used to specifically and covalently attach the detectable label to the ACP fusion protein, either in vitro or in a cell or on the surface of a cell (in vivo). This allows the detection and characterization of the ACP fusion protein in vivo or in vitro. The term in vivo includes labeling in all compartments of a cell as well as of ACP fusion proteins pointing to the extracellular space. The method can be compared to the applications of the green fluorescent protein (GFP) which is also genetically fused to the protein of interest and allows its investigation in the living cell. The disadvantage of GFP and its mutants is that it is principally limited to the use of the natural occurring fluorophore present in GFP. The labeling inside a cell (in vivo) may be used also after fixation of the cell by common fixation procedures which have only minor impact on the functional structure of proteins and thus leave the ACP functional with respect to labeling by a phosphopantetheinyl moiety.

The use of a labeled CoA derivative, wherein the phosphopantetheinyl moiety carries an affinity tag such as biotin which can be transferred to the ACP fusion protein, allows the invention to be used to transfer an affinity tag to the ACP fusion protein, thereby allowing the fusion protein to be bound by a binding partner of the affinity tag. By way of example, the addition of CoA substrates labeled with an affinity tag such as biotin and ACPS to cell extracts (bacterial or eukaryotic) expressing an ACP fusion protein or to purified ACP fusion proteins, will lead to the covalent modification of the fusion protein with the affinity tag. This will then allow the isolation of the fusion protein using the interaction between the affinity tag and its binding partner, e.g. in the case of biotin, with immobilized avidin or streptavidin. If the label is linked to the ACP fusion protein via a linker group R containing a cleavable bond, such as a disulfide bridge, or if the linker is photocleavable, the ACP fusion protein can be released from the affinity tag after its isolation.

The use of a labeled CoA derivative, wherein the phosphopantetheinyl moiety carries a label which can be transferred to the ACP fusion protein and which is capable of generating reactive radicals, such as hydroxyl radicals, upon exposure to an external stimulus, allows the study of conformations of the protein of interest and of proteins in the vicinity. The generated radicals can inactivate the ACP fusion proteins as well as those proteins that are in close proximity of the ACP fusion protein, allowing the study the role of these proteins. Examples of such labels are tethered metal-chelate complexes that produce hydroxyl radicals upon exposure to $H_2O_2$ and ascorbate, and chromophores such as malachite green that produce hydroxyl radicals upon laser irradiation. The use of chromophores and lasers to generate hydroxyl radicals is also known in the art as chromophore assisted laser induced inactivation (CALI), for example as described by Jay et al., 1998. CALI is a method that is used to specifically inactivate certain proteins within a cell in a time-controlled and spatially-resolved manner and which is based upon the spatial neighbourhood of a chromophore and a protein. Upon laser irradiation the chromophore generates hydroxyl radicals, which inactivate all proteins within and only within about 100 nm of the chromophore. So far, the chromophore is brought in the spatial neighbourhood of the protein of interest by micro-injecting chromophore-labeled antibodies specific to the protein of interest. In the present invention, labeling ACP fusion proteins with chromophores such as malachite green and subsequent laser irradiation would allow to inactivate the ACP fusion protein as well as those proteins that interact with the ACP fusion protein in a time-controlled and spatially-resolved manner. The method can be applied both in vivo or in vitro.

In a similar manner, ACP fusion proteins can be labeled with tethered metal-chelates and the ACP fusion protein and those proteins that interact with the ACP fusion protein can be inactivated in a specific manner upon exposure to $H_2O_2$ and ascorbate. The method can not only be used to study the function of an ACP fusion protein or those that are in close proximity of the ACP fusion protein, but also to identify those proteins that are in close proximity of a ACP fusion protein. Here, proteins which are in close proximity of the ACP fusion protein can be identified as such by either detecting fragments of that protein by a specific antibody, by the disappearance of those proteins on a high-resolution 2D-electrophoresis gels or by identification of the cleaved protein fragments via separation and sequencing techniques such as mass spectrometry or protein sequencing by N-terminal degradation.

The use of a labeled CoA derivative, wherein the phosphopantetheinyl moiety carries a ligand which can be transferred to the ACP fusion protein, allows the invention to be used to specifically attach the ligands and binding partners of the ligand, such as proteins, to the ACP fusion protein. If the ligand binds to another protein Y and the dimerization of the protein Y with the labeled ACP fusion protein leads to a biological function or a measurable signal, the biological function or the measured signal depends on the addition of the labeled ACP fusion protein. If ACP is coupled to proteins displayed on cell surfaces the interaction with the ligand can mediate contacts with other molecules modified by the ligand, including biomolecules, either individually or as part of other cells, of tissue, and of intact organisms modified by the ligand.

The use of a labeled CoA derivative, wherein the phosphopantetheinyl moiety is covalently attached to the surface of a carrier, or wherein the label is a molecule that can be bound non-covalently by another molecule that is itself attached to the surface, allows the invention to be used to construct protein arrays on a solid support. An example for the latter approach is where the label is biotin and the molecule attached to the surface is streptavidin or avidin. Possible examples for a carrier are a glass side, a microtiter plate or any functionalized polymer. The CoA derivative used as a substrate is immobilized on the carrier via its label, and the subsequent ACPS-catalyzed reaction of an ACP fusion protein immobilizes such fusion protein on the carrier by the transfer of the label to the fusion protein. Spotting (different) ACP fusion proteins together with ACPS in a spatially resolved manner on the carrier pretreated with the corresponding CoA derivative allows the creation of protein arrays.

The use of a labeled CoA derivative, wherein the phosphopantetheinyl moiety is covalently attached to a label which is a molecule that can cross-link to other proteins, allows the invention to be used to study interactions of the protein of interest in a suitable environment. Examples of such cross-linkers are molecules containing functional groups such as maleimides, active esters or azides, and others known to those proficient in the art, e.g. those described in Nadeau et al., 2002. Contacting such labeled CoA derivatives in the presence of ACPS with ACP fusion proteins that interact with other proteins (in vivo or in vitro) can lead to the covalent cross-linking of the ACP fusion protein with its interacting protein via the label. This allows the identification of the protein interacting with the ACP fusion protein.

The use of a labeled CoA derivative, wherein the phosphopantetheinyl moiety carries a ligand which can be transferred to an ACP fusion protein consisting of ACP and a membrane receptor and which allows detection of the labeled receptor. This labeling of the cell surface receptor allows to observe receptor internalization. A particular application is the investigation of the internalization of receptor proteins after binding of a ligand, for example by a drug, a drug lead or a tentative drug lead. The receptor internalization can be detected by various methods, e.g. by microscopic detection of translocation of the label from the cell membrane to the cell interior or by changes in the fluorescence characteristics of the label upon transfer to the intracellular milieu. Such changes can also be detected without microscopic tools and may be facilitated by the addition of a quencher to the extracellular medium.

The use of a labeled CoA derivative, wherein the phosphopantetheinyl moiety carries a ligand which can be directly detected by electron microscopy, e.g. electron dense nanoparticles. Another application of the phosphopantetheinyl moiety for electron microscopy detection is based on labels used as photosensitizers such as eosin to oxidize upon illumination aromatic amines, such as dianisidine, into an electron dense precipitate which can then be detected by electron microscopy.

By way of example, embodiments of the present invention will now be described in more detail with reference to the accompanying figures.

EXAMPLES

The following examples and experimental procedures are set forth so as to provide those of ordinary skill in the art with a complete disclosure and description of how to practice the invention, and are not intended to limit the scope of the invention.

Synthesis of CoA-Bt

To a solution of biotin-maleimide 1 (1 mg, 0.0022 mmol) in 100 µl DMF, a solution of coenzyme A disodium salt (1.79 mg, 0.0022 mmol, 1 eq.) in 90 µl DMF and 10 µl 50 mM Tris-Cl pH 7.5 is added. The mixture is stirred for 4 hours at room temperature. It is then diluted with $CH_3CN/H_2O$ 1:4, and aliquots of 500 µl are injected on a preparative HPLC column: Gradient (A=$H_2O$ 99%, $CH_3CN$ 1%, 50 mM $NH_4OAc$/B=$CH_3CN$) from A/B 95:5 to A/B 80:20 in 2 min, to A/B 68:32 in 7 min, to A/B 20:80 in 2 min, then back to A/B 95:5. The retention time of the CoA-biotin is 6.5 min. Fractions containing the desired product are concentrated in vacuo, dissolved in DMSO, and an analytical amount injected to control the purity. The pure fractions are combined. The concentration of CoA-biotin is determined by absorption at 260 nm ($\epsilon$(adenine, 260 nm)=15'300 [$M^{-1}$ $cm^{-1}$]). The yield of CoA-Bt is 0.895 mg (33%).

ESI-MS (m/z) calculated 1217.296 [M(−1)], found 1217.2657 [M(−1)]

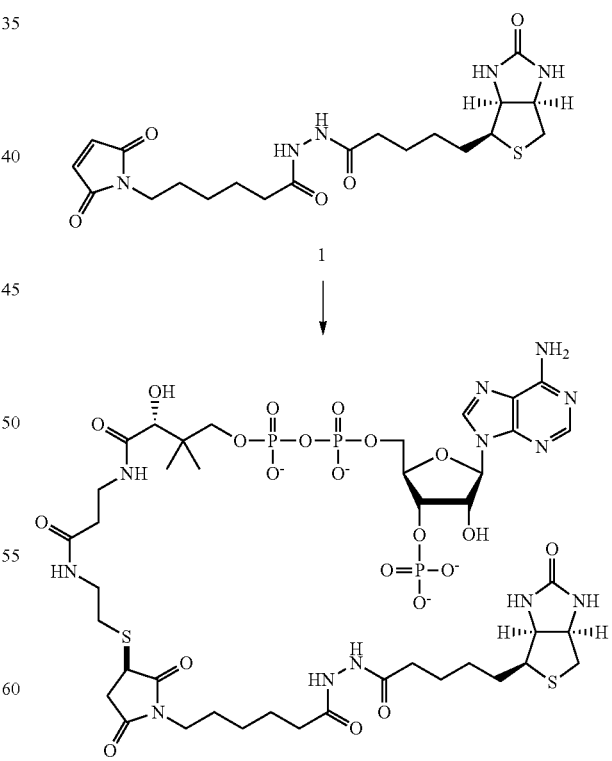

Synthesis of CoA-Dg

To a solution of N-(ε-maleimidocaproic acid) hydrazide 2 (1 mg, 0.0044 mmol) in 50 µl DMF, a solution of coenzyme A disodium salt (3.6 mg, 0.0044 mmol, 1 eq.) in a DMF/buffer mixture (70 μl DMF/30 μl 50 mM Tris Cl, pH 7.5) is added. The reaction is followed by analytical HPLC (detection at 260 nm) to verify the completion of the reaction. Subsequently, a solution of 3-amino-3-deoxydigoxigenin hemisuccinamide succinimidyl ester (2.6 mg, 0.0044 mmol, 1 eq.) dissolved in 50 μl DMF and 10 μl Et$_3$N is added, and the reaction mixture stirred for 4 hours at room temperature. The reaction is submitted to preparative HPLC and fractions containing the desired product are concentrated in vacuo, dissolved in DMSO, and analyzed by analytical HPLC for purity. Fractions containing pure product are combined. The concentration of CoA-Dg is determined using the extinction coefficient of adenine ($\epsilon$(adenine, 260 nm)=15'300 [M$^{-1}$ cm$^{-1}$]). The yield of CoA-Dg is 2.37 mg (37%).

ESI-MS (m/z) calculated 1462.3707 [M(−1)], found 1462.481 [M(−1)].

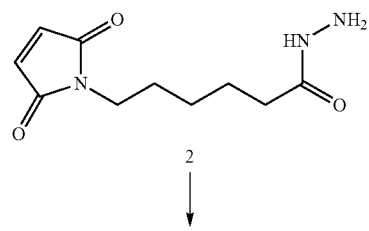

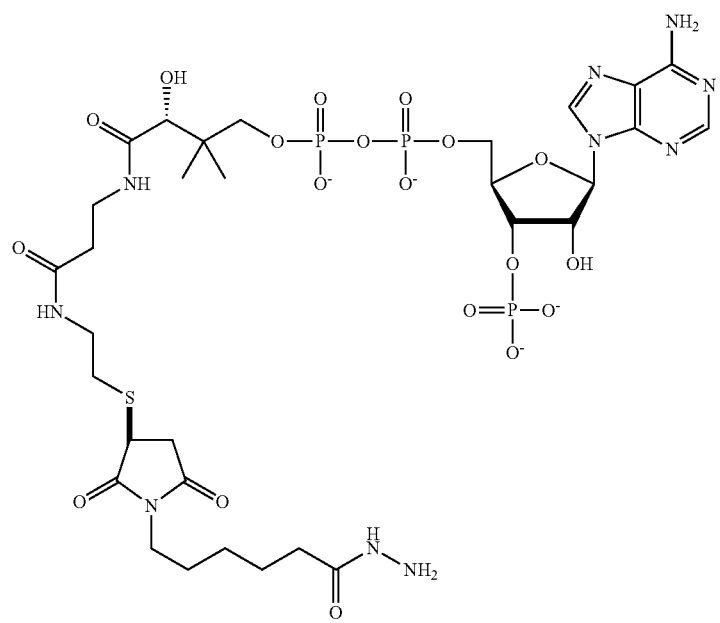

-continued

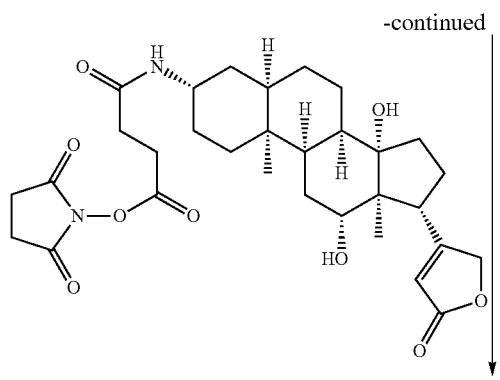

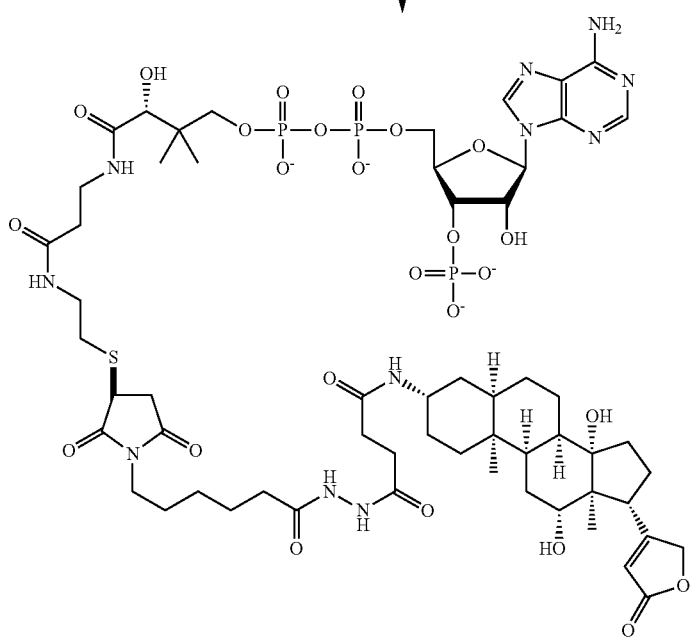

Synthesis of CoA-Cy3

To a solution of Cy3-maleimide 3 (Pharmacia, 1 mg, 0.00126 mmol) in 100 μl DMF, a solution of coenzyme A disodium salt (1.05 mg, 0.00126 mmol, 1 eq.) in 90 μl DMF and 10 μl 50 mM Tris.Cl pH 7.5 is added. The mixture is stirred for 4 hours at room temperature. It is then diluted with CH$_3$CN/H$_2$O 1:4, and aliquots of 500 μl are injected on a preparative HPLC column: Gradient from NB 95:5 to NB 90:10 in 2 min, to A/B 65:35 in 15 min, to NB 20:80 in 2 min, then back to A/B 95:5 (A and B see preceding example). The retention time of CoA-Cy3 is 10 min. Fractions containing the desired product are concentrated in vacuo, dissolved in DMSO, and an analytical amount injected to control the purity. The pure fractions are combined. The concentration of CoA-Cy3 is determined by absorption at 549 nm (ε (549 nm)=150'000 [M$^{-1}$ cm$^{-1}$]). The yield of CoA-Cy3 is 0.847 mg (44%).

ESI-MS (m/z) calculated 1519.370 [M(−1)], found 1519.3071 [M(−1)].

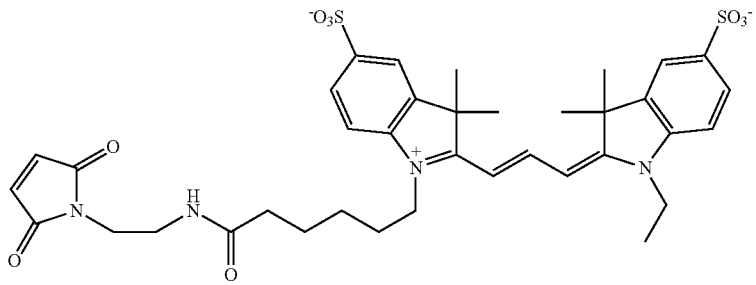

3

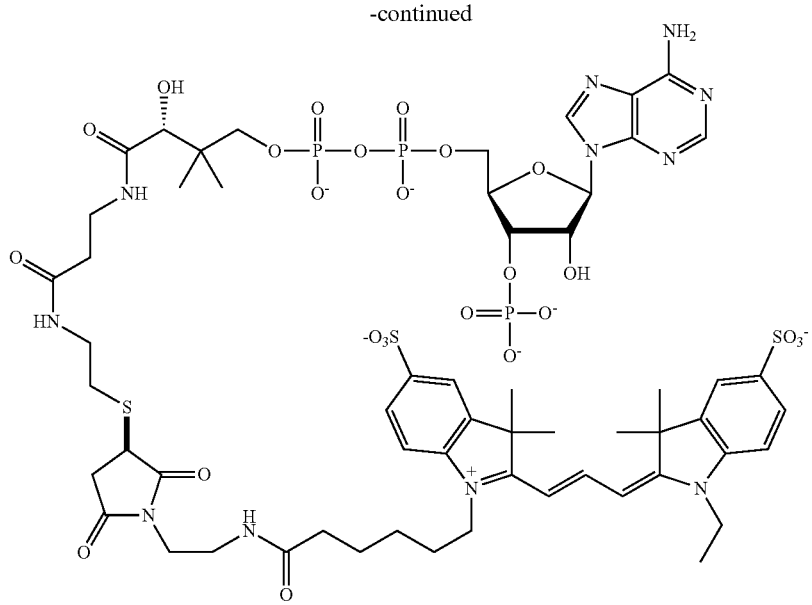
Synthesis of CoA-Cy5
The synthesis of CoA-Cy5 starting with the Cy5-maleimide 4 (1 mg, 0.00122 mmol) is performed as described for CoA-Cy3. The concentration of CoA-Cy5 is determined using the extinction coefficient of Cy5 ($\epsilon$ (646 nm)=250'000 [$M^{-1}$ $cm^{-1}$]). The yield of CoA-Cy5 is 0.828 mg (44%).
ESI-MS (m/z) calculated 1545.386 [M(−1)] and 772.189 [M(−2)], found 771.6524 [M(−2)].
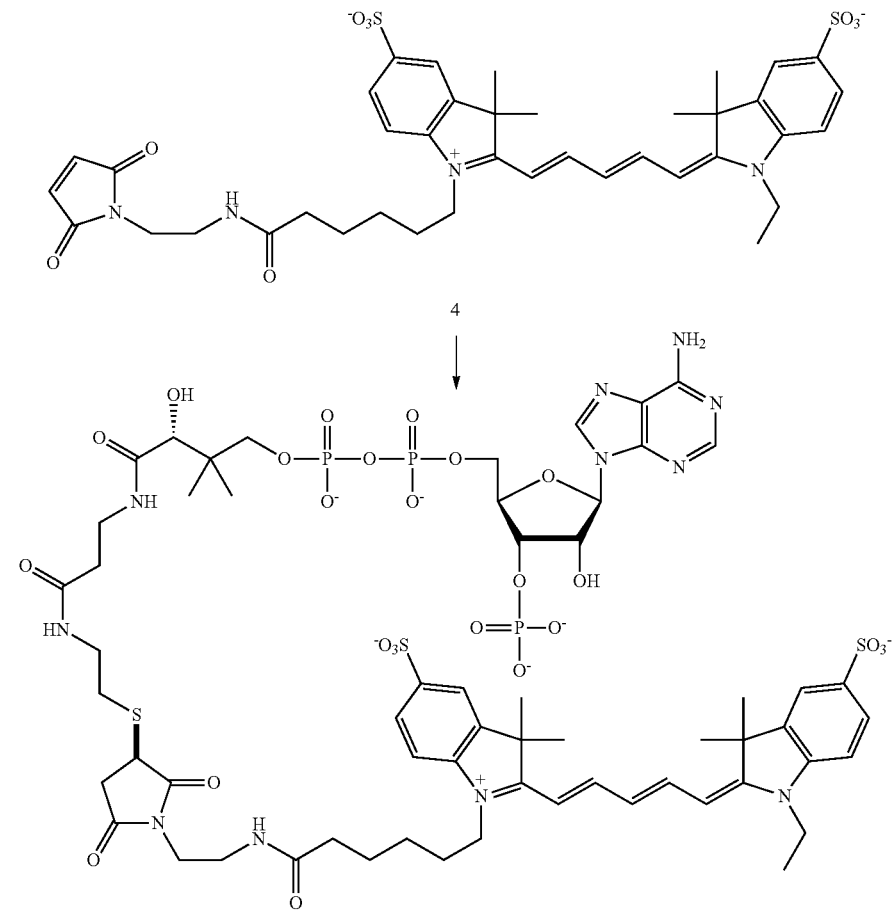

Cloning, Expression and Purification of 6xHis-ACPS

The XL1-blue *E. coli* ACPS gene is amplified by single colony PCR and cloned in a pET-15b plasmid (Novagen) using the forward primer 5'-TCT GGT CAT ATG GCA ATA TTA GGT TTA GGC ACG G-3' with the NdeI restriction site (underlined), and the backward primer 5'-TCA AGT CTC GAG TTA ACT TTC AAT AAT TAC CGT GGC A-3' with the XhoI restriction site (underlined). The sequence of the peptide (originating from the plasmid pET-15b) fused to the N-terminus of *E. coli* ACPS is (in single letter code) MGSSH-HHHHHSSGLVPRGSH followed by the first amino acid of ACPS, a methionine. This fusion protein is designated 6xHis-ACPS.

Liquid cultures of BL21 *E. coli* cells containing a pET-15b (Novagen) based expression vector encoding 6xHis-ACPS are grown to an optical density $OD_{600nm}$ of 0.6. Expression of 6xHis-ACPS is induced by adding IPTG to a final concentration of 1 mM. After incubation for 3.5 hours at 220 rpm at 24° C., the culture is centrifuged for 10 minutes at 3000 g at 4° C. The pellet is resuspended in 10 ml extract-buffer (150 mM NaCl, 5 mM imidazole, 50 mM $KH_2PO_4$, pH 8.0), and PMSF and aprotimine are added to a final concentration of 1 mM and 2 µg/ml respectively. Lysozyme is added to 1 ring/ml, and the mixture is incubated for 15 minutes on ice and inverted several times. Then it is sonicated for 10 minutes (95% Power, 50% Duty). DNase I is added to a final concentration of 0.01 mg/ml. After 30 minutes at 4° C., the mixture is centrifuged for 10 minutes at 18'000 rpm.

For the purification of the protein, 350 µl of Ni-NTA, previously washed three times with extract buffer, are added to the lysate. The mixture is incubated 20 minutes on ice and mixed several times. The extract mixture is then added to a polypropylene column, which is allowed to drain. The column is washed with 5×400 µl DNA elution buffer (10 mM Tris.Cl, pH 8.5), then with 2×5 ml wash buffer (300 mM NaCl, 10 mM imidazole, 50 mM $KH_2PO_4$, pH 7.5). To elute the protein, elution buffer (300 mM NaCl, 150 mM imidazole, pH 7.5) is added to the column, incubated for 10 minutes, and then the flow-through is collected. Elution is continued stepwise with 150 µl elution buffer until no more protein is detectable in a Bradford assay. Finally the combined eluates are dialysed overnight in dialysis buffer (50 mM HEPES, 30% glycerol, pH 7.2) to remove the residual salts. The pure 6xHis-ACPS (MW 16.215 kDa) is aliquoted and stored at −80° C. The concentration is determined by a Bradford assay to be 37.6 µM. Yield 0.912 mg per liter of BL21 *E. coli* cell culture.

Cloning, Expression and Purification of 6xHis-ACP

The XL1-blue *E. coli* ACP gene is amplified by single colony PCR and cloned in a pET-15b plasmid (Novagen) using the forward primer 5'-GT CGG TAT CATATG AGC ACT ATC GAA GAA CG-3' with the NdeI restriction site (underlined) and the backward primer 5'-TCA TGC GGATCC TTA CGC CTG GTG GCC GTT G-3' with the BamHI restriction site (underlined). The sequence of the peptide fused to the N-terminus of *E. coli* ACP (yielding 6xHis-ACP) is (in single letter code) MGSSHHHHHHSS-GLVPRGSH followed by the first amino acid of ACP, a methionine.

Liquid cultures of BL21 *E. coli* cells containing a pET-15b (Novagen) based expression vector encoding 6xHis-ACP are grown to an optical density $OD_{600nm}$ of 0.6. Expression of 6xHis-ACP is induced by adding IPTG to a final concentration of 1 mM. After incubation for 3.5 hours at 220 rpm at 37° C., the culture is centrifuged for 10 minutes at 3000 g at 4° C. The pellet is treated exactly as described in the above experiment for the purification of 6xHis-ACPS. The concentration of 6xHis-ACP (MW 10.802 kDa) is determined by a Bradford assay to be 188 µM. Yield: 3.1 mg per liter of BL21 *E. coli* cell culture. To determine the ratio between apo- and holo-6xHis-ACP, purified 6xHis-ACP is analyzed by ESI-MS (pos. mode) using a Q-T of-Ultima (Micromass/Waters), optionally coupled to Cap-LC (Waters), chromatography on Xterra RP-C4 column (Waters, 5 µm, 0.32×50 mm; flow 8 µl/min) and deconvolution by MaxEnt1-software. ESI-MS of the mixture demonstrates that the preparation contains a mixture of holo- and apo-ACP. The mass of purified apo-6xHis-ACP without the first methionine is found to be 10.6720 kDa (calculated 10.6716 kDa), and that of holo-6xHis ACP to be 11.012 kDa (calculated 11.0119 kDa). LC-ESI-MS allows the identification and integration of the peaks corresponding to the holo- and apo-form. The percentage of the holo-form is determined to be 16% (retention time 11.77 min), and that of the apo-form to be 84% (retention time 14.16 min).

Expression and Purification of 6xHis-ACP-ha

The sequence of the peptide fused to the N-terminus of *E. coli* ACP is (in single letter code) MGSSHHHHHHSS-GLVPRGSH followed by the first amino acid of ACP, a methionine, and the sequence of the peptide fused to the C-terminus of *E. coli* ACP is (in single letter code) TSRSY-PYDVPDYARW (yielding 6xHis-ACP-ha).

Liquid cultures of BL21 (DE3) *E. coli* cells containing a pET-15b based expression vector encoding 6xHis-ACP-ha are grown to an optical density $OD_{600nm}$ of 0.6. Expression of 6xHis-ACP-ha is induced by adding IPTG to a final concentration of 1 mM. After incubation for 3 hours at 220 rpm at 24° C., the culture is centrifuged for 10 minutes at 3000 g at 4° C. 6xHis-ACP is then purified as described for the purification of 6xHis-AcpS. The concentration of 6xHis-ACP-ha (MW 12.65 kDa) is determined by Bradford assay to be 400 µM, and the total yield of protein is 10 mg per liter of shake-flask culture.

In Vitro Biotinylation of 6xHis-ACP Using CoA-Bt and 6xHis-ACPS

Purified 6xHis-ACP (1 µM) is incubated with 6xHis-ACPS (0.2 µM) and $MgCl_2$ (10 mM) in reaction buffer (43 µl, 50 mM Tris Cl, pH 8.8) at room temperature. An aliquot of 7.5 µl is taken for analysis. CoA-Bt is added to a final concentration of 5 µM. Aliquots of 7.5 µl are taken at defined times. The aliquots are quenched for 30 seconds with coenzyme A (1 mM final concentration), and 8.2 µl SDS-buffer 2× are added. The samples are heated for 2 minutes at 95° C. The biotinylated 6xHis-ACP is detected by Western-blotting, using a streptavidin-horseradish peroxidase conjugate (NEN) and a chemiluminescent peroxidase substrate (Renaissance reagent plus, NEN). The western blot is analyzed using an image station (Kodak 440). As controls, samples containing each protein alone, and samples containing only one of the two proteins and CoA-Bt are also prepared and analyzed for biotinylation as above in order to check the background and to check the specificity of the reaction. The biotinylation depends on the presence of all three components.

Quantification of Biotinylation of 6xHis-ACP via Gel Shift Assay

Purified 6xHis-ACP (3 µM) is incubated at RT with CoA-Bt (10 µM) and purified 6xHis-ACPS (5 µM) in a final volume of 50 µl reaction buffer (50 mM Tris.Cl, pH 8.8, 10 mM $MgCl_2$). After 30 minutes of incubation, the mixture is dialyzed overnight against TBS (10 mM Tris.Cl, 150 mM NaCl, pH 7.9) to remove any excess CoA-Bt. Aliquots of the reaction are incubated with streptavidin for 1 h at a final concentration of 0.6 µg/µl. 2×SDS sample buffer containing only 2% SDS is added to samples, and SDS-PAGE is performed directly without heating the sample. Proteins are detected by Coomassie staining, and the degree of biotinylation is estimated by comparison of the band intensities with samples containing the identical amount of 6xHis-ACP not biotinylated and not incubated with streptavidin.

Competition Assays between CoA and CoA-label

Purified 6xHis-AcpS (0.4 µM) is incubated at RT with either CoA-Bt or CoA-Dg (2 µM), variable amounts of CoA (0, 2, 4, 8, 12, 20, 40, 80 µM) and purified 6xHis-ACP-ha (0.4 µM) in 20 µl reaction buffer (50 mM Tris.Cl, pH 7.5, 10 mM $MgCl_2$). After 25 minutes, each sample is quenched by addition of 20 µl of 2×SDS sample buffer and heated at 95° C. for 2 minutes. Labeled 6xHis-ACP-ha is detected by Western-blotting using either a streptavidin-horseradish peroxidase conjugate (dilution 1:12500) or an anti-digoxigenin antibody-horseradish peroxidase conjugate (dilution 1:500) and a chemiluminescent peroxidase substrate. Signal intensities at 0 µM CoA are arbitrary set to 1 for each experiment.

Labeling of Aga2-ACP on the Surface of Yeast Cells

The sequence of AGA2 is amplified from yeast genomic DNA and inserted in the yeast expression vector pRS314 behind the $P_{CUP1}$-promoter sequence using the EcoRI and SalI restriction sites introduced at the ends of the PCR fragment. ACP is cloned in frame behind AGA2 using a SalI and an Acc651 restriction site introduced by the PCR amplification of the ACP sequence. ACP is extended by a sequence encoding the HA-epitope. The sequence connecting Aga2p and ACP reads: FVDEMLYFQGM. The last residue of Aga2p and the first residue of ACP are underlined. The C-terminal sequence of ACP including the HA-epitope reads: QAYPYDVPDYAG. The last residue of ACP is underlined. Yeast strain EBY100 (MATa ura3-52 trp1 leu2Δ1 his3Δ200 pep4::HIS3 can1 GAL pIU211:URA3) (Invitrogen, Carlsbad, Calif.) expressing Aga1p from the $P_{GAL1}$-promoter and Aga2-ACP from the $P_{CUP1}$-promoter are grown in 10 ml of selective medium containing 2% galactose and 0.1 mM copper to an $OD_{600}$ of 1.4 $OD_{600}$ units of the cells are washed with 2 ml water and resuspended in 0.2 ml labeling buffer (50 mM Tris Cl pH 8.8, 100 mM NaCl, 10 mM $MgCl_2$). CoA substrate and 6xHis-ACPS are added to a final concentration of 10 and 1 µM, respectively. Labeling is stopped after 20 min at RT by diluting the reaction into 2 ml PBS. The cells are washed four times with 2 ml of PBS and either subjected to fluorescence microscopy directly or after a 20 min incubation in 0.2 ml of Qdot™incubation buffer containing 20 nM Qdot™605 streptavidin conjugate (Milan Analytica AG, Switzerland) followed by washing the cells in four times 2 ml of PBS. Cells are inspected with a Zeiss Axiovert 135 fluorescence microscope (Carl Zeiss, Göttingen, Germany) using a 63× oil (1.4 numerical aperture) objective.

Labeling of ACP-NK1 Fusion Protein Displayed on HEK293 Cells

For the transient expression of ACP-NK1, the signal sequence of the 5-$HT_3$-receptor ($Sig_{5HT3}$) is fused to the N terminus of ACP via a short DYV linker and NK1 is fused to the C terminus of ACP via a short TS linker. In the resulting construct, a FLAG tag and a 6xHis tag is also attached to the C terminus of NK1. The corresponding gene of the fusion protein is inserted into the NheI and BamHI sites of the vector pCEP4 (Invitrogen). HEK293 cells are grown in DMEM/F2 (Dulbecco's modified Eagle medium, GIBCO BRL) supplemented with 2:2% fetal calf serum (GIBCO, BRL). Transient transfection is performed as described (Nat Biotechnol 21, 86-89 (2003)) and the HEK293 cells are co-transfected with vectors expressing ACP-NK1 and a nuclear targeted EGEP (EGFP-$NLS_3$). After 24 h, cells are incubated for 10 min at room temperature with 500 µl of PBS buffer containing $MgCl_2$ (10 mM), 6xHis-AcpS (1 µM) and either CoA-Cy3, CoA-Cy5 or CoA-Bt (each 5 µM). The cells are then washed three times with PBS to remove any excess substrate and directly analyzed by laser-scanning confocal fluorescence microscopy when labeled with Cy3 or Cy5. Biotinylated cells are incubated with FluoroLink™ Cy5-labeled streptavidin (Amersham Biosciences) at concentrations of 1 µg/ml in PBS before being washed three times with PBS. Laser-scanning confocal micrographs are recorded using a 488 nm argon/krypton laser line; a 543 nm HeNe laser line or a 633 nm HeNe laser line on a Zeiss LSM 510 microscope (Carl Zeiss AG, Göttingen, Germany) with a 63× water (1.2 numerical aperture) objective. Scanning speed and laser intensity are adjusted to avoid photobleaching of the fluorescent probes, and damage or morphological changes of the cells. Fluorescence is analyzed in the channels sensitive to GFP and sensitive to the respective dye. For each cell sample tested a clear nuclear labeling is observed in the GFP channel, and a clear membrane labelling is observed in the cell membrane region after labelling with CoA-Cy3, after labelling with CoA-Cy5, and after labelling with CoA-Bt and subsequent staining with Streptavidin-Cy5. No membrane staining is observed for non-transfected cells showing no nuclear expression of GFP, indicating a specific labeling of ACP-NK1 with Cy3, Cy5 and biotin, respectively. The ACP-NK1 receptor transiently expressed in HE293 cells is co-stained in a further experiment with CoA-Cy5 and with tetramethylrhodamine-labeled substance P(SP-rho), the natural ligand of $NK_1$. Both substance stain exclusively the membrane area and lead to identical stained regions. The reversal of the SP-rho staining by an excess of unlabeled substance P within one minute furthermore proves the specificity of the labelling and also the functionality of ACP-NK1 with respect to ligand binding.

REFERENCES

R B Ali et al., *Molecular and Cellular Biology*, 18, 1660-1669 (1998)

A M Gehring et al., *Chemistry & Biology* 4, 17-25 (1997)

S N Ho et al., *Nature* 382, 822-6 (1996)

R Hori and N Baichoo in *Protein-Protein interactions: A molecular cloning manual*; Ed. E Golemis, Cold Spring Harbor Laboratory Press; pp. 288-311 (2002)

D G Jay and T Sakurai, *Biochim. Biophys. Acta* M39-48 (1999)

P A Kolodziej and R A Young, *Methods Enzymol.* 194, 508-19, (1991)

R H Lambalot et al., *Chemistry & Biology* 3, 923-936 (1996)

R H Lambalot and C T Walsh, *J. Biol. Chem.* 270, 24658-24661 (1995)

J Ma and M Ptashne, *Cell* 51, 113-9, (1987)

O W Nadeau and G M Carlson in *Protein-Protein interactions: a molecular cloning manual*; Ed. E Golemis, Cold Spring Harbor Laboratory Press; pp. 75-92 (2002)

J H Nunberg et al., *Cell* 19, 355-364 (1980).

M Rawlings and J E Cronan, *J. Biol. Chem.* 267, 5751-5754 (1992)

J Schultz and M Carlson, *Mol Cell Biol* 7, 3637-45 (1987).

The invention claimed is:

1. A labeled CoA type substrate of the formula (I) or (II):

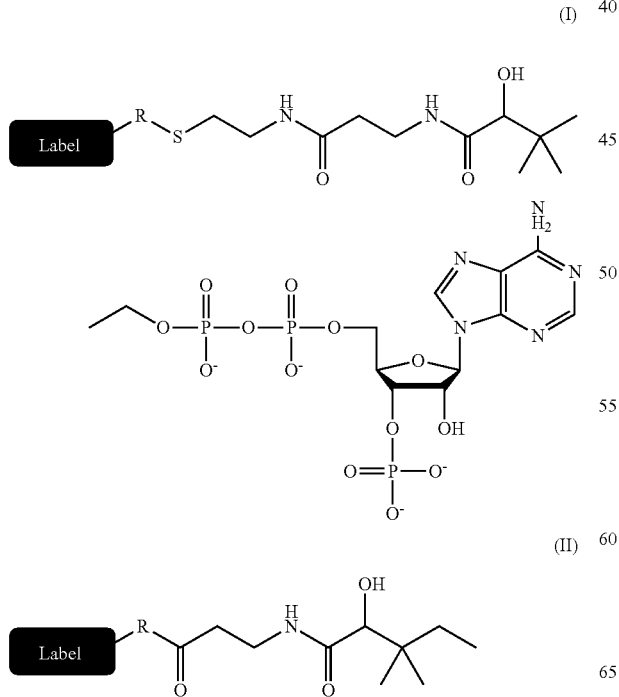

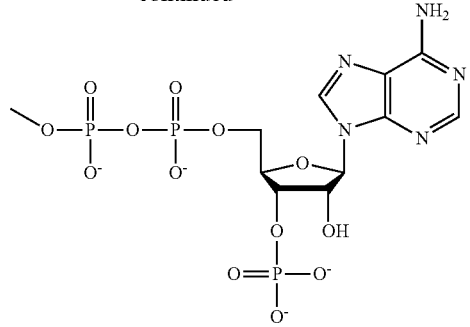

wherein R is a linker group bridging the coenzyme A and the label; and wherein R is a straight or branched chain alkylene group with 1 to 300 carbon atoms, wherein (a) R has at least 3 carbon atoms wherein every third carbon atom is replaced by oxygen; or (b) one or more carbon atoms are replaced by nitrogen carrying a hydrogen atom, and the adjacent carbon atoms are substituted by oxo, representing an amide function —NH—CO—; or (c) one or more carbon atoms are replaced by oxygen, and the adjacent carbon atoms are substituted by oxo, representing an ester function —O—CO—; or (d) the bond between two adjacent carbon atoms is a double or a triple bond, representing a function —CH=CH— or —C≡C—; or (e) one or more carbon atoms are replaced by a phenylene, a saturated or unsaturated cycloalkylene, a saturated or unsaturated bicycloakylene, a bridging heteraromatic or a bridging saturated or unsaturated heterocyclyl group; or (f) two adjacent carbon atoms are replaced by a disulfide linkage —S—S—; or a combination of two or more, especially two, alkylene and/or modified alkylene groups as defined under (a) to (f) hereinbefore, optionally containing substituents; and "Label" is a label molecule suitable for the detection and/or manipulation of a fusion protein in a system designed for detecting and/or manipulating the label.

2. A labeled CoA type substrate according to claim 1 wherein "Label" is selected from the group consisting of (1) a spectroscopic probe;
(2) a radioactively labeled molecule;
(3) a molecule which is one part of a specific binding pair which is capable of specifically binding to a partner;
(4) a molecule that is suspected to interact with other biomolecules;
(5) a library of molecules that are suspected to interact with other biomolecules;
(6) a molecule which is capable of crosslinking to other biomolecules;
(7) a molecule which is capable of generating hydroxyl radicals upon exposure to $H_2O_2$ and ascorbate;
(8) a molecule which is capable of generating reactive radicals upon irradiation with light;
(9) a molecule covalently attached to a solid support;
(10) a nucleic acid or a derivative thereof capable of undergoing base-pairing with its complementary strand;
(11) a lipid or other hydrophobic molecule with membrane-inserting properties;
(12) a biomolecule with desirable enzymatic, chemical or physical properties; and
(13) a molecule possessing a combination of any of the properties (1) to (12).

3. A labeled CoA type substrate according to claim 1 wherein "Label" is selected from biotin, digoxigenin, Cy-3 and Cy-5.

4. A method for detecting and/or manipulating a protein of interest using a labeled CoA type substrate according to claim 1, which comprises:

(a) contacting a fusion protein comprising (i) a protein of interest consisting of at least 12 amino acids and up to 2,000 amino acids and (ii) an acyl carrier protein (ACP) or a fragment thereof containing a serine residue to which a phosphopantetheine moiety of a labeled coenzyme A (Co A) type substrate according to claim 1 is attachable; by means of a holo-acyl carrier protein synthase (ACPS) or a homologue thereof selected from the group consisting of EntD, Sfp, Psf-1, Gsp, LYS5, Bli, Lpal4, and NshC, (b) transferring the label from the CoA type substrate to the fusion protein in the presence of ACPS; and (c) detecting and/or further manipulating the labeled fusion protein obtained, using the label in a system designed for detecting and/or manipulating the label.

* * * * *